United States Patent [19]
Dubroff

[11] Patent Number: 5,273,751
[45] Date of Patent: * Dec. 28, 1993

[54] COMPOSITION FOR PREVENTING CLOUDING OF PAOSTERIOR CAPSULE AFTER EXTRACAPSULAR CATARACT EYE SURGERY AND METHOD OF PERFORMING CATARACT SURGERY

[76] Inventor: Seymour Dubroff, 3806 Thornapple St., Chevy Chase, Md. 20815

[*] Notice: The portion of the term of this patent subsequent to Mar. 20, 2007 has been disclaimed.

[21] Appl. No.: 773,266

[22] Filed: Oct. 9, 1991

Related U.S. Application Data

[60] Division of Ser. No. 483,719, Feb. 23, 1990, Pat. No. 5,080,647, which is a continuation-in-part of Ser. No. 173,625, Mar. 25, 1988, Pat. No. 4,909,784.

[51] Int. Cl.$^5$ .............. A61F 2/14; A01N 25/04; A61M 1/00
[52] U.S. Cl. .............. 424/427; 424/423; 514/912; 604/22; 604/27; 604/28; 604/30; 604/31; 604/35; 604/36; 604/38; 604/39; 604/40; 604/41; 604/42; 604/43; 604/45; 604/48; 604/49
[58] Field of Search .............. 604/22, 27, 28, 30, 604/31, 35, 36, 38, 39, 40, 41, 42, 43, 45, 48, 49; 514/912; 424/422, 423, 427

[56] References Cited

U.S. PATENT DOCUMENTS

| | | | |
|---|---|---|---|
| 4,819,617 | 4/1989 | Goldberg et al. | 536/98 |
| 4,909,784 | 3/1990 | Dubroff | 604/49 |
| 4,965,253 | 10/1990 | Goldberg et al. | 514/54 |
| 5,013,295 | 5/1991 | Dubroff | 604/38 |

Primary Examiner—Paul R. Michl
Assistant Examiner—Carlos Azpuru

[57] ABSTRACT

The present invention relates to compositions for killing undifferentiated epithelial cells during cataract surgery on an eye to prevent posterior capsule clouding after the surgery and to a method for performing cataract surgery on an eye including injecting a cell-killing substance between the anterior capsule and the natural lens prior to removing the natural lens from the eye. The cell-killing substance is preferably an acid or base adjusted aqueous solution having a pH in the range between about 1.0 to below 6.5 or about above 7.5 to 14.0; or a hypotonic solution having a salinity less than 0.9% or a pH adjusted hypotonic solution having a salinity less than 0.9% and a pH either below 6.5 or above 7.5. The compositions of the present invention also incorporates a viscoelastic material, a dye or a mixture thereof, in combination with the cell-killing substance.

24 Claims, 1 Drawing Sheet

COMPOSITION FOR PREVENTING CLOUDING OF PAOSTERIOR CAPSULE AFTER EXTRACAPSULAR CATARACT EYE SURGERY AND METHOD OF PERFORMING CATARACT SURGERY

RELATED APPLICATIONS

This application is a divisional application of application Ser. No. 07/483,719, filed Feb. 23, 1990, now U.S. Pat. No. 5,080,647 which is a continuation-in-part of Ser. No. 07/173,625, filed Mar. 25, 1988 now U.S. Pat. No. 4,909,784.

BACKGROUND OF THE INVENTION

1. Field of the Invention

The present invention pertains to cataract surgery and, more particularly, to the prevention of clouding of the posterior capsule after extracapsular cataract extraction.

2. Discussion of the Prior Art

Clouding of the posterior capsule after extracapsular cataract extraction, with or without the implant of an intraocular lens, has been a principal, later occurring, complication of such extracapsular cataract surgery. During cataract surgery, it is preferable to extract the natural lens while leaving the posterior portion of the lens capsule intact in front of the vitreous cavity of the eye to provide a barrier to prevent anterior movement or loss of the vitreous which fills the cavity and to also provide a support for an intraocular lens implanted in the posterior chamber. If the natural lens is removed intact with the capsule, referred to as intracapsular cataract extraction, the vitreous can move through the pupil causing vitreous loss and increasing the chances of complications, such as glaucoma, corneal opacity, displacement of an intraocular lens, retinal hemorrhage, holes, breaks and detachment, and cystoid macula edema.

In many cases after extracapsular cataract extraction, with or without the implant of an intraocular lens, the posterior capsule becomes opacified or clouded due to migration of proliferating undifferentiated epithelial cells into the optical zone which, clustered, form Elschnig's pearls. Along with Elschnig's pearls, visual acuity is also reduced by invading fibroblasts through metaplasia developing into myoepithelial fibers, lens fibers, collagen, fibrosis and Sommering rings. This opacification or clouding of the posterior capsule, referred to as secondary cataract, occurs in a large percentage of extracapsular cataract extractions and is a primary cause of post operative complications.

One procedure to remove secondary cataracts is discussion using a needle or scissors to punch or cut a hole in the posterior capsule. Another procedure includes the use of a YAG laser focused through the pupil to open the posterior capsule. Such procedures, referred to as posterior capsulotomy, remove the opacification to improve sight; however, they also create the adverse effects discussed above with respect to intracapsular cataract extraction due to the removal of the barrier to vitreous movement.

Other attempts to prevent clouding of the posterior capsule include constructing intraocular lenses to produce barriers to movement of the undifferentiated epithelial cells from the equator of the posterior capsule toward the optical zone; however, such intraocular lenses have been difficult to implant in the posterior capsule and have not created effective barriers to prevent clouding.

Still another attempt to prevent proliferation of lens epithelial cells after extracapsular cataract extraction is shown in U.S. Pat. No. 4,432,751, to Emery et al, which instills monoclonal antibodies specific to lens epithelial cells into the anterior chamber to cause lysis or other damage to the lens epithelial cells and prevent the cells from multiplying and covering the posterior lens capsule.

Accordingly, there is a great need for a manner in which to prevent opacification of the posterior capsule, particularly in view of the great number of cataract surgeries performed each year and the substantial likelihood of most individuals having cataract surgery due to the natural forming of cataracts in the natural lens with aging. As noted above, the preferable procedure for cataract surgery is extracapsular cataract extraction; and, thus, much effort has been directed toward overcoming the late capsule clouding complication associated with such cataract surgery.

SUMMARY OF THE INVENTION

Accordingly, it is a primary object of the present invention to prevent clouding of the posterior capsule after extracapsular cataract extraction without requiring removal, puncturing or discussion of the posterior capsule.

A further object of the present invention is to prevent clouding of the posterior capsule after extracapsular cataract extraction by killing remaining undifferentiated epithelial cells by either osmotic cellular destruction in a hypotonic environment and/or lysis by destructive pH alteration.

Another object of the present invention is to provide a method of performing cataract surgery on an eye to prevent capsule clouding after the surgery by injecting a cell-killing substance between the capsule and the natural lens and thereafter removing the natural lens from the eye.

Yet another object of the present invention is to provide a cell-killing substance of a hypotonic (hypoosmotic) solution, a pH altering solution having a pH either below 6.5 or above 7.5, or a hypotonic solution having a pH either below 6.5 or above 7.5, for injection between the capsule and the natural lens of an eye prior to removal of the natural lens to kill the undifferentiated epithelial cells by osmotic cellular destruction and/or by destructive pH alteration.

It is still another object of the present invention to utilize a viscoelastic material in admixture with the cell-killing substance to facilitate the spread of the admixture to assure contact of the cell-killing substance with all undifferentiated epithelial cells and to promote increased contact time between the cell-killing substance and the undifferentiated epithelial cells.

It is still another object of the present invention to incorporate a dye in admixture with the cell-killing substance so that the area of administration of the resultant colored mixture is visually apparent.

Yet an additional object of the present invention is to place a viscoelastic material in the anterior chamber of an eye prior to injecting a cell-killing substance between the capsule and the natural lens such that the viscoelastic material prevents any cell-killing substance escaping from the capsule opening from reaching the corneal endothelium.

The present invention is characterized by a novel composition for administration between the anterior capsule and the lens during cataract surgery. This composition includes a cell-killing substance having properties to kill undifferentiated lens epithelial cells by osmolysis and/or destructive pH alteration and optionally contains a viscoelastic material, a dye or both.

The present invention is further characterized in a method of performing cataract surgery on an eye to prevent capsule clouding after the surgery comprising the steps of: (1) injecting the novel composition including a cell-killing substance between the capsule and the natural lens, the substance having properties to kill undifferentiated epithelial cells; (2) maintaining the cell-killing substance in contact with the undifferentiated epithelial cells for a sufficient period of time to kill these cells by osmotic cellular destruction or destructive pH alteration, and removing the natural lens from the eye.

Some of the advantages of the present invention over prior art methods of preventing or eliminating capsule clouding are that the composition and method of the present invention can be utilized along with the procedures of normal cataract surgery requiring only a single additional procedure, no difficult or complex surgical procedures are required, safety is assured by the use of viscoelastic materials and the nature of the composition assures the killing or destruction of all undifferentiated epithelial cells.

Other objects and advantages of the present invention will become apparent from the following description of the preferred embodiment taken in conjunction with the accompanying drawings.

DESCRIPTION OF THE PREFERRED EMBODIMENT

Figure 1:
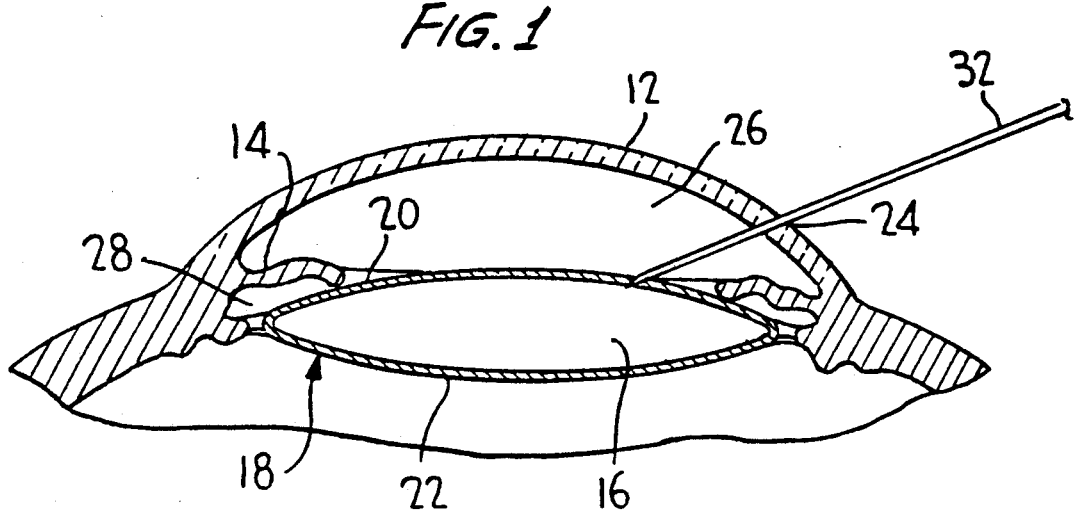
FIG. 1 is a cross-section of an eye illustrating injection of a cell-killing substance in accordance with the present invention.
Figure 2:
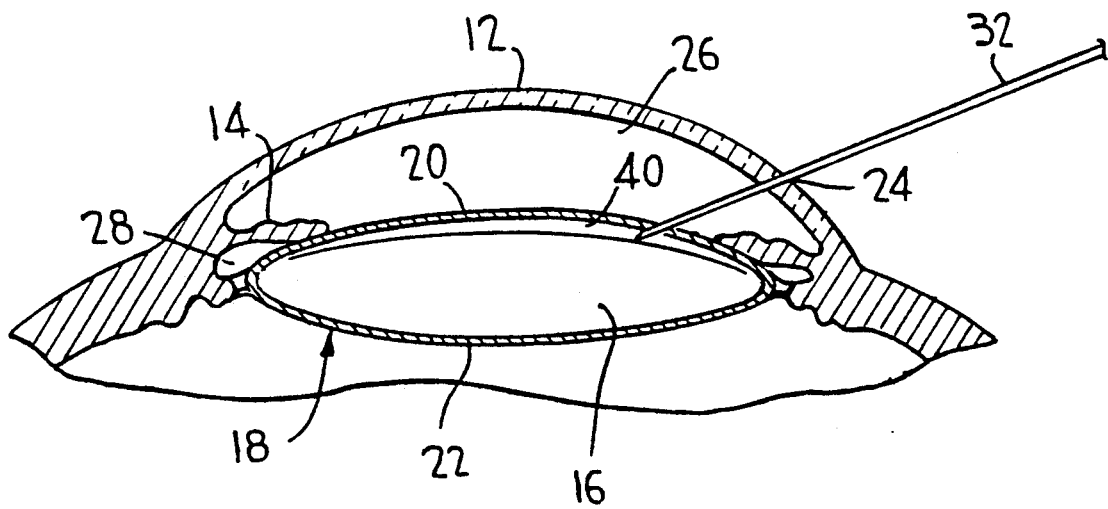
FIG. 2 is a cross-section of an eye after injection of the cell-killing substance in accordance with the present invention.

The present invention will be explained with respect to FIGS. 1 and 2 which illustrate an eye including a cornea 12, an iris 14, a natural lens 16 and a capsule 18 surrounding the lens formed of an anterior capsule segment 20 and a posterior capsule segment 22. In conventional extracapsular cataract surgery, an incision 24 is made in the cornea and an anterior capsulotomy is performed to remove a portion of the anterior segment 20 of the capsule. Thereafter, the natural lens 16 is removed; and, if desired, an intraocular lens can be positioned in either the anterior chamber 26, defined as the region between the cornea and the iris, or the posterior chamber 28, defined as the region behind the iris, posterior chamber intraocular lenses being positioned normally in the posterior capsule 22 or in the sulcus.

In accordance with the present invention, after the incision 24 is made, a syringe is inserted therethrough having a hollow hypodermic needle 32. The surgeon punctures the anterior segment 20 of the capsule 18 with the needle 32; and, once the needle 32 is so positioned, the syringe is operated to force a cell-killing substance between the capsule 18 and the lens 16 to form a fluid pocket 40, the substance at least completely surrounding the anterior surface of the lens to completely contact the anterior capsule segment 20. The cell-killing substance is maintained in contact with the undifferentiated epithelial cells for a period sufficient to kill all of the undifferentiated epithelial cells. A particularly effective syringe for introducing the cell-killing substance is shown and described in application Ser. No. 07/173,625 and includes an aspirating tube having an open distal end disposed adjacent the capsule to evacuate any cell-killing substance escaping from the capsule. Furthermore, to ensure that the cell-killing substance does not come into contact with the cornea or other eye tissues, the anterior chamber 26 is filled with a viscoelastic material, such as VISCOAT produced by Cilco.

The cell-killing substances destroy the undifferentiated epithelial cells by osmolysis or by destructive pH alteration. Upon contacting the undifferentiated epithelial cells with a hypotonic solution cell-killing substance, the cells continuously absorb the cell-killing substance by osmosis until the cells are destroyed by bursting or exploding within approximately thirty seconds. The undifferentiated epithelial cells undergo a destructive pH change by contacting the cells with a pH adjusted solution thereby killing the cells within approximately a minute by altering the normal chemical reactions required for metabolic activity essential for the life of the cell. Thus, the cell-killing substance should be maintained in contact with the epithelial cells for a period of time sufficient to complete destruction of the cells by osmolysis or by altered pH lysis. The cell-killing substances of the present invention include hypotonic solutions, pH adjusted solutions, or pH adjusted hypotonic solutions. Hypotonic (hypo-osmotic) solutions are defined herein as any solution having an osmotic pressure lower than the pressure naturally existing in the undifferentiated epithelial cells. Thus, any solution providing an osmotic pressure below normal saline solution can be employed in accordance with the present invention. Organic hypotonic solutions can be utilized including, but not limited to, alcohols, ketones, ethers or aldehydes.

Preferred hypotonic solutions include distilled water or water having a salinity less than 0.9%. Preferably the hypotonic solution injected as a cell-killing substance has a salinity of from 0 to 0.6%, it being found that salinity percentages of from 0 to 0.3 are highly effective. Suitable salts such as NaCl or other pharmaceutically acceptable salts are utilized to effect the desired percentage of salinity.

The pH adjusted solutions of the present invention have either a pH in the acidic pH range between approximately 1.0 to below 6.5 or in the basic pH range between approximately above 7.5 to 14.0. The preferred pH adjusted solutions used as cell-killing substances possess a pH in either of the following two ranges: $3.5 \leq pH < 6.4$ or $7.8 \leq pH \leq 10.5$. More preferably the pH adjusted solutions possess a pH ranging either between 5.8 to 6.2 or between 8.0 to 8.4, while the most preferable pH adjusted solutions are pH adjusted aqueous solution having a pH of either approximately 6.0 or 8.2.

The pH adjusted solutions used as pH altering cell-killing substances are organic or inorganic, aqueous preferably and are produced by adding either basic or acid components to organic or inorganic diluents. The acidic pH adjusted solutions are produced by adding an appropriate amount of HCl, preferably, or other ophthalmically acceptable acids to a diluent such as water. The basic pH adjusted solutions are produced by adding an appropriate amount of NaOH, preferably, or other ophthalmically acceptable bases to a diluent such as water. Other ophthalmically acceptable acids for use in the present invention to prepare the pH adjusted solutions include but are not limited to: mineral acids and organic acids such as $H_2SO_4$, $HNO_3$, $H_3PO_4$, acetic, proprionic, oxalic, maleic, benzoic acids and the like. Other ophthalmically acceptable bases include but are not limited to: alkali or alkaline earth hydroxides, carbonates or bicarbonates or the like, preferably potassium hydroxide.

The hypotonic solutions for use in the present invention can also be pH adjusted to enhance the ability of the solution to destroy undifferentiated epithelial cells. The previously discussed hypotonic solutions are pH adjusted with the aforementioned acids or bases utilized to adjust the pH in the pH adjusted solutions. The pH adjusted hypotonic solutions formed in this manner have a pH either below 6.5 or above 7.5 and have the same preferred pH ranges as the pH adjusted solutions. The pH adjusted hypotonic solutions destroy undifferentiated epithelial cells by both osmolysis and by destructive pH alteration to assure that all cells are destroyed.

The pocket 40 is essentially a "potential" space in that the capsule is contracted tightly around the lens. Since all undifferentiated epithelial cells must be contacted by the cell-killing substance, the potential space must be expanded in all areas between the lens and the anterior capsule segment to form pocket 40, and it has been found that use of a viscoelastic material in admixture with the cell-killing substance, preferably premixed prior to injection, facilitates the even flow of the admixture to form fluid pocket 40 and assures that all areas of the anterior surface of lens 16 and the posterior surface of anterior capsule segment 20 come into contact with the cell-killing substance. The admixture of the viscoelastic material with the cell-killing substance facilitates the spread of the admixture onto the surface of the outer periphery of lens 16. Furthermore, the use of the viscoelastic material increases the contact time between the cell-killing substance and the undifferentiated epithelial cells through retention of the cell-killing substance against the epithelial cells by the viscoelastic material.

Preferred viscoelastic materials for use in admixture with the cell-killing substances of the instant invention include, but are not limited to, HEALON, VISCOAT, ORCOLON, methylcellulose, methyl hyaluronate, polyacrylamide and polymethacrylamide. The viscoelastic material is preferably utilized in amounts ranging from 0.5 to 5.0%, preferably 1 to 3% by weight of the cell-killing substance injected into fluid pocket 40.

As pointed out above, it is important to contact all undifferentiated epithelial cells with the cell-killing substance; however, it is extremely difficult for the surgeons to visually determine that the cell-killing substance has completely filled the pocket and expanded all portions of the anterior capsule segment. Accordingly, a dye is admixed with the cell-killing substance prior to or after injection of the cell-killing substance between the inner surface of the anterior capsule 20 and the lens 16. The use of such a dye provides visually recognizable color to the injected solution so that a surgeon can visually determine the extent of the flow of the injected solution between the anterior capsule 20 and the lens 16. The surgeon can thus visually confirm that the cell-killing substance has completely filled the capsule space forming fluid pocket 40 between the anterior capsule 20 and the lens 16 so that all of the anterior capsule 20 comes in fluid contact with the cell-killing substance.

Preferred dyes for use in combination with the cell-killing substance of the present invention include, but are not limited to, methylene blue and triptolene blue. It has been determined that blue, purple and green dyes provide the best contrast for visualization during insertion of the cell-killing substance; however, any dye providing sufficient contrast to show the extent of the area of coverage of the cell-killing substance between the anterior capsule 20 and the lens 16 can be utilized. When utilized, the aforementioned preferred colors also provide the best contrast with cataracts which appear to be amber in color.

The dyes should be utilized in amounts to effectively provide color to the cell-killing substance upon visual examination. It is preferable to incorporate a dye in extreme dilution to provide a visually apparent amount, preferably from 0.1 to 10 parts per million of the cell-killing substance.

The cell-killing substances may be administered alone, in combination with a dye or a viscoelastic material, or in combination with both a dye and a viscoelastic material in accordance with the present invention. Any combination of the aforementioned substances, namely the cell-killing substance alone or together with the dye and/or the viscoelastic material, is preferably administered by injection in an amount of less than 2.0 cc, most preferably less than 1.5 cc, between the lens 16 and the anterior segment 20 of the capsule 18 such that there is minimal opportunity for the substance to escape from the capsule while still providing full fluid contact of the injected cell-killing substance solution between the inner anterior capsule surface and the lens surface, preferably at least 0.5 cc.

In use, a syringe is filled with the cell-killing substance, which may be optionally admixed with a dye and/or a viscoelastic material; and, as a piston is forced into a chamber in the syringe, the cell-killing substance or mixture thereof is forced through needle 32 between the anterior capsule 20 and the natural lens 16 with sufficient pressure to surround the lens and kill epithelial cells therein by osmotic pressure. The injected cell-killing substance may completely surround the lens 16 between both the anterior capsule 20 and the posterior capsule 22; however as illustrated in FIG. 2, it is important only that a sufficient amount of solution be injected to form a fluid pocket 40 allowing the cell-killing substance to contact all portions of the anterior capsule segment since undifferentiated epithelial cells only habitat in the lens capsule 18 between the anterior capsule 20 and the lens 16. Any cell-killing substance inadvertently escaping from the capsule through the puncture is constrained to move along the needle and through incision 24 due to the viscoelastic in the anterior chamber 26 or can be collected by an aspirating tube. Accordingly, the cell-killing substance is prevented from contact with any eye tissue.

In view of the above, it will be appreciated that the method of preventing capsule clouding according to the present invention is extremely simple and efficacious in that the capsule is used to confine the cell-killing substance but is not a living cell and, therefore, is not affected by the cell-killing substance.

Inasmuch as the present invention is subject to many variations and modifications in detail, it is intended that all subject matter discussed above or shown in the accompanying drawings be interpreted as illustrative and not in a limiting sense.

What is claimed is:

1. A composition for administration between an anterior capsule and a lens comprising a pH adjusted solution having a pH in a range between approximately 1.0 to below 6.5 or a pH in a range between approximately above 7.5 to 14, a visually apparent amount of a dye and 0.5 to 5.0% by weight of a viscoelastic material.

2. The composition of claim 1 wherein said solution comprises a mixture of water and an acid.

3. The composition of claim 2 wherein said acid is HCl.

4. The composition of claim 1 wherein said solution comprises a mixture of water and a base.

5. The composition of claim 4 wherein said base is NaOH.

6. The composition of claim 1 wherein said dye is blue.

7. The composition of claim 1 wherein said visually apparent amount of said dye is 0.1 to 10 ppm.

8. The composition of claim 1 wherein said solution has a pH ranging between 5.8 to 6.2 or between 8.0 to 8.4.

9. A composition for administration between an anterior capsule and a lens comprising 0.5 to 5.0% by weight of a viscoelastic material and a cell-killing substance having properties to kill undifferentiated epithelial cells.

10. The composition of claim 9 additionally comprising a dye.

11. A composition for administration between an anterior capsule and a lens comprising a dye and a cell-killing substance having properties to kill undifferentiated epithelial cells.

12. A composition for administration into an eye between an anterior capsule and a natural lens comprising a hypotonic solution having a salinity less than 0.9% and having properties to kill undifferentiated epithelial cells, a visually apparent amount of a dye and 0.5 to 5.0% by weight of a viscoelastic material.

13. The composition of claim 12 wherein said solution has a pH below 6.5 or above 7.5.

14. The composition of claim 12 wherein said solution has a pH in the range from between 5.8 to 6.2 or between 8.0 to 8.4.

15. The composition of claim 12 wherein said solution has a salinity less than 0.6%.

16. A system for preventing clouding of the posterior capsule after extracapsular cataract extraction by killing lens epithelial cells while the natural lens remains in the capsule characterized in a syringe having an injection chamber filled with a substance having properties to kill lens epithelial cells and 0.5 to 5.0% by weight of a viscoelastic material, a piston movably disposed in said injection chamber, and a needle communicating with said injection chamber and having a configuration to inject said substance between the anterior capsule and the natural lens through an open distal end of the needle when said piston is moved in said injection chamber whereby the epithelial cells are killed while the natural lens remains in the capsule.

17. The system as recited in claim 16 wherein said substance comprises a solution having a salinity less than 0.9% to kill the epithelial cells by osmotic pressure.

18. The system as recited in claim 17 wherein said solution has a pH in the range between approximately 1.0 to below 6.5 or a pH in a range between approximately 7.5 to 14.

19. The system as recited in claim 16 wherein the injection chamber is additionally filled with a visually apparent amount of dye.

20. The system as recited in claim 16 further characterized by a viscoelastic material placed in the anterior chamber of the eye preventing any of the substance escaping from the capsule from reaching the corneal endothelium.

21. A system for preventing clouding of the posterior capsule after extracapsular cataract extraction by killing lens epithelial cells while the natural lens remains in the capsule characterized in a syringe having an injection chamber filled with a substance having properties to kill lens epithelial cells and a visually apparent amount of dye, a piston movably disposed in said injection chamber, and a needle communicating with said injection chamber and having a configuration to inject said substance between the anterior capsule and the natural lens through an open distal end of the needle when said piston is moved in said injection chamber whereby the epithelial cells are killed while the natural lens remains in the capsule.

22. The system as recited in claim 21 wherein said substance comprises a solution having a salinity less than 0.9% to kill the epithelial cells by osmotic pressure.

23. The system as recited in claim 22 wherein said solution has a pH in the range between approximately 1.0 to below 6.5 or a pH in a range between approximately 7.5 to 14.

24. The system as recited in claim 21 further characterized by a viscoelastic material placed in the anterior chamber of the eye preventing any of the substance escaping from the capsule from reaching the corneal endothelium.

* * * * *